United States Patent
Brown et al.

(10) Patent No.: US 8,007,707 B1
(45) Date of Patent: Aug. 30, 2011

(54) METHOD OF MANUFACTURE AIR FRESHENING ARTICLE

(75) Inventors: Douglas S. Brown, Toledo, OH (US); Jeffrey A. Smith, Toledo, OH (US)

(73) Assignee: Fresh Products, Inc., Toledo, OH (US)

( * ) Notice: Subject to any disclaimer, the term of this patent is extended or adjusted under 35 U.S.C. 154(b) by 186 days.

(21) Appl. No.: 12/152,627

(22) Filed: May 15, 2008

Related U.S. Application Data

(60) Provisional application No. 60/930,202, filed on May 15, 2007.

(51) Int. Cl.
*E03D 13/00* (2006.01)

(52) U.S. Cl. .................... 264/331.11; 4/222.1

(58) Field of Classification Search ............ 264/78, 264/273, 331.11, 331.15; 4/222.1
See application file for complete search history.

(56) References Cited

U.S. PATENT DOCUMENTS

| | | | |
|---|---|---|---|
| 3,760,429 A * | 9/1973 | Brownstein ............... 4/222.1 |
| 3,804,796 A * | 4/1974 | Alexandre ............ 264/331.15 |
| 4,095,031 A * | 6/1978 | Engle ..................... 523/102 |
| 4,405,509 A | 9/1983 | Rogers et al. |
| 4,440,542 A | 4/1984 | Foley |
| 4,515,909 A | 5/1985 | Sawano et al. |
| 4,761,437 A | 8/1988 | Christie |
| 5,019,434 A * | 5/1991 | Matsumoto ............. 428/35.7 |
| 5,087,273 A | 2/1992 | Ward |
| 5,139,864 A | 8/1992 | Lindauer |
| 5,150,722 A | 9/1992 | Rutherford |
| 5,188,755 A | 2/1993 | Chang |
| 5,336,424 A | 8/1994 | Van Vlahakis et al. |
| 5,398,347 A * | 3/1995 | Luedtke et al. ............ 4/301 |
| 5,472,712 A | 12/1995 | Oshlack et al. |
| 5,489,415 A | 2/1996 | Van Vlahakis et al. |
| 5,580,578 A | 12/1996 | Oshlack et al. |
| 5,639,476 A | 6/1997 | Oshlack et al. |
| D393,896 S * | 4/1998 | Wagner et al. ........... D23/261 |
| 5,813,058 A * | 9/1998 | Quigley et al. ............ 4/309 |
| 5,958,334 A | 9/1999 | Haddon |
| 6,079,975 A | 6/2000 | Conover |
| 6,207,236 B1 | 3/2001 | Araki et al. |
| 6,213,409 B1 | 4/2001 | Warren et al. |
| 6,517,759 B1 * | 2/2003 | Ferenc et al. ............ 264/211 |
| 6,703,012 B1 | 3/2004 | White |
| 6,730,311 B2 | 5/2004 | Maleeny et al. |
| 6,920,648 B1 * | 7/2005 | Suski et al. .............. 4/309 |
| 7,202,201 B1 | 4/2007 | Williams |
| 2005/0144711 A1 * | 7/2005 | Valadez et al. ........... 4/309 |
| 2005/0245671 A1 | 11/2005 | Moon et al. |
| 2007/0023539 A1 | 2/2007 | Brown et al. |
| 2008/0292509 A1 * | 11/2008 | D'Amico ............... 422/125 |

* cited by examiner

*Primary Examiner* — Jill Heitbrink
(74) *Attorney, Agent, or Firm* — Knobbe Martens Olson & Bear, LLP

(57) ABSTRACT

An air freshening article, such as a deodorizing urinal screen, includes a body that is formed from a fragranced plastic that includes a plastic loaded with a fragrance material. The fragrance material is included in an amount of at least 15% by weight of the fragranced plastic. A method of producing a deodorizing urinal screen includes a fragrance loading stage in which a plastic is loaded with a fragrance material to produce a fragranced plastic. The fragranced plastic includes at least 15 wt % fragrance material. In a molding stage subsequent to the fragrance loading stage, the fragranced plastic is molded into the urinal screen.

20 Claims, 2 Drawing Sheets

METHOD OF MANUFACTURE AIR FRESHENING ARTICLE

CROSS-REFERENCE TO RELATED APPLICATIONS

This application claims the benefit of U.S. Provisional Application No. 60/930,202, filed May 15, 2007, the disclosure of which is incorporated herein by reference.

BACKGROUND OF THE INVENTION

This invention relates in general to air fresheners for masking or suppressing undesirable odors. In particular, this invention relates to an improved structure for an air freshening article and to an improved method of manufacturing same.

There are many environments in which it is desirable to mask or suppress undesirable odors. For example, it is known that in restrooms, urinals may emit offensive odors. Additionally, in many other environments (typically relatively small enclosed environments), it is desirable to provide fresh or pleasant odors. For example, it is known to provide fresh or pleasant odors within the relatively small enclosed environment of a vehicle.

A variety of air freshening articles are known in the art to mask or suppress undesirable odors and to provide fresh or pleasant odors. For example, it is known to manufacture urinal screens for use in urinals in restrooms that are formed from a plastic material having an outer surface that is coated with a fragrant material. Although known air freshening articles such as this have been effective, it would be desirable to provide an improved structure for an air freshening article and an improved method of manufacturing same.

SUMMARY OF THE INVENTION

This invention relates to an improved structure for an air freshening article and to an improved method of manufacturing same.

The deodorizing article includes a body that is formed from a fragranced plastic that includes a plastic loaded with a fragrance material. The fragrance material is included in an amount of at least about 5% by weight of the fragranced plastic.

A method of producing a deodorizing urinal screen includes a fragrance loading stage in which a plastic is loaded with a fragrance material to produce a fragranced plastic. In a molding stage subsequent to the fragrance loading stage, the fragranced plastic is molded into the urinal screen which includes a screen body sized to be disposed over a urinal drain.

Various additional aspects of the invention will become apparent to those skilled in the art from the following detailed description of the preferred embodiment, when read in light of the accompanying drawing.

DETAILED DESCRIPTION OF THE PREFERRED EMBODIMENT

Figure 1:
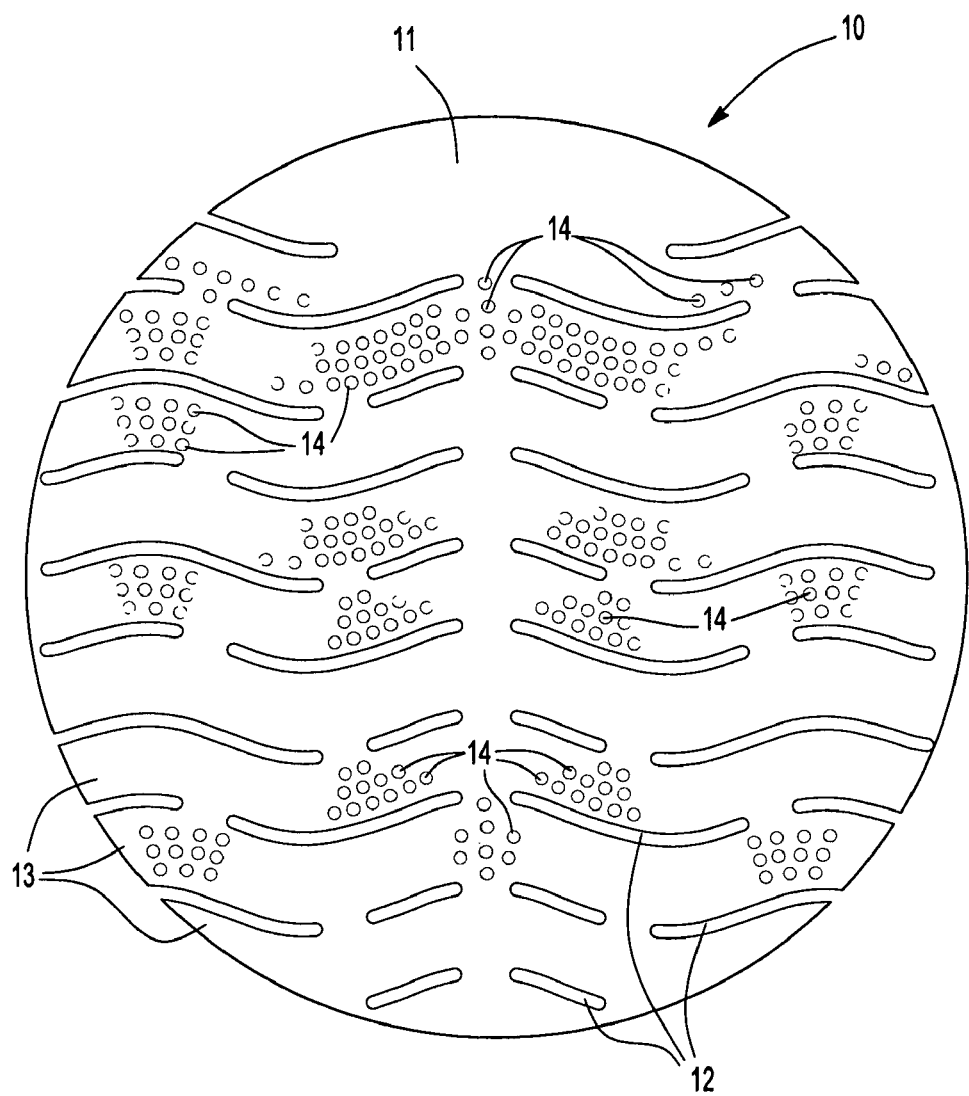
FIG. 1 is a plan view of an air freshening article in accordance with this invention.

Referring now to the drawings, there is illustrated in FIG. 1 an air freshening article, indicated generally at 10, in accordance with this invention. The illustrated air freshening article 10 is, in large measure, conventional in the art and is intended merely to illustrate one environment in which this invention may be used. Thus, the scope of this invention is not intended to be limited for use with the specific structure of the air freshening article 10 illustrated in FIG. 1. On the contrary, as will become apparent below, this invention may be used in any desired environment for the purposes described below.

The illustrated air freshening article 10 is a urinal screen that is adapted for use in a conventional urinal (not shown), such as commonly found in public restrooms. Alternatively, the air freshening article could be incorporated into or onto a product for automatically flushing a toilet or urinal. Additionally, this invention may be embodied as any one of a wide variety of structures that are commonly used for air freshening applications. For example, this invention may be embodied in any of the following applications: cleaning blocks; toilet deodorant/cleaning blocks; sink drain strainer/cleaner/deodorizer; dry wick deodorants that hang loosely or are supported in dispensers; dry solid room deodorizers in fan-assisted cabinets; closet deodorizers; small space deodorizers; vehicle deodorizers; hot air hand dryer deodorizers; and closet air freshener. However, this list of applications for this invention is merely illustrative and is not intended to limit the scope of this invention.

The urinal screen 10 illustrated in FIG. 1 includes a body 11 that, in the illustrated embodiment, is generally flat and circular in shape. However, the body 11 may have any desired size and shape. The illustrated body 11 has a plurality of openings 12 formed therethrough. The body 11 may be formed having any desired number of such openings 12 or, alternatively, no openings 12 at all if desired. The openings 12 can have any desired size and shape and may be provided at any location or locations on the body 11. The illustrated body 11 also has a plurality of notches 13 formed in an outer peripheral surface thereof. The body 11 may be formed having any desired number of such notches 13 or, alternatively, no notches 13 at all if desired. The notches 13 can have any desired size and shape and may be provided at any location or locations on the outer peripheral surface of the body 11. Typically, the body 11 is shaped such that it extends over a drain portion of the urinal. This allows the urinal screen 10 to prevent solid materials from undesirably entering into the drain portion of the urinal.

The openings 12 and notches 13 permit the screen 10 to conform to the drain portion of the urinal to provide a good fit. Additionally, the openings 12 and notches 13 function to permit fluids through the screen 10 to the drain portion to prevent the screen 10 from floating above or about the drain portion. Prior art designs without such notches and/or openings floated over the drain portion, thus permitting solids to enter the drain portion.

The design of the screen 10 helps to keep the urinal, the urinal user and the restroom area clean. Protrusions 14 formed vertically with respect to the screen 10 help to break up the force of the urine stream and reduce its strength, thus keeping it in the urinal. Preferably, the protrusions 14 are located substantially across the screen 10, thus increasing its surface area. In contrast, flat surfaces reflect back the urine, leading to coated clothing and surrounding areas.

The body 11 of the urinal screen 10 is formed from a plastic material that is loaded with a fragrance material. As used herein, the term "plastic" means any type of polymer, including synthetic or natural polymers. The polymers that may be suitable include both thermoplastic and thermoset polymers. Some examples of polymers that may be suitable are synthetic resins. Some particular examples of thermoplastic resins that may be suitable for forming the body 11 of the urinal screen 10 include ethylene vinyl acetate (EVA), polyvinyl chloride (PVC), polyethylene (PE), polypropylene (PP), polymethylpentene (MPX), ethylene-(meth)acrylate ester copolymers, acrylic-type vinyl resins such as polymethyl methacrylate (PMMA), styrene-type vinyl resins such as polystyrene (PS), acrylonitrile-butadiene-styrene (ABS) copolymers, acrylonitrile-styrene (AS) copolymers, other vinyl resins such as polyvinyl acetate, polyvinylidene chloride (PVDC), polyvinyl alcohol (PVA), and polytetrafluoroethylene (PTFE), polyester resins such as polybutylene terephthalate (PBT) and polyethylene terephthalate (PET), polyamide resins such as nylon 6, nylon 66, nylon 610, nylon 11, and nylon 12, polyoxyalkylene resins such as polyacetal (POM), and other thermoplastic resins such as polycarbonates (PC), modified polyphenylene ethers (modified PPE), polyvinyl acetates (PVAC), polysulfones (PSU), polyethersulfones (PES), polyphenylene sulfides (PPS), polyarylates (PAR), polyamideimides (PAT), polyetherimides (PEI), polyetheretherketones (PEEK), polyimides (PI), as well as copolymers of the preceding. Combinations of different plastics can also be used to produce the body 11 of the urinal screen 10.

In some embodiments, the plastic material that is used to form the body 11 of the urinal screen 10 has a melting point not greater than about 250° F., more particularly not greater than about 225° F., and even more particularly not greater than about 200° F. The use of a low melting polymer allows lower molding temperatures during the manufacture of the body 11 of the urinal screen 10. These lower molding temperatures can reduce the amount of loss of fragrance that can occur during the molding process. For example, ethylene vinyl acetate has a melting point of about 176° F. Other examples of low melting polymers include very low density polyethylene, ethylene plastomers, ethylene-acrylic acid or ethylene-methacrylic acid copolymers or terpolymers, ethylene homopolymers or ethylene copolymers, blends thereof, and others that are known in the art.

In some embodiments, the plastic material that is used to form the body 11 of the urinal screen 10 allows the production of an air freshening article that is compliant with VOC regulations, for example the VOC regulations for a "toilet and urinal care product" category. For example, the ability of the plastic material to hold and release a variety of different fragrance materials can enable a VOC-compliant urinal screen that releases VOC-compliant aroma chemicals at a level equivalent to or better than other "air fresheners", and significantly better than other urinal screens.

The plastic material that is used to form the body 11 of the urinal screen 10 is loaded with a fragrance material to produce what may be called a fragranced plastic. The loading can be any type of association of the fragrance material with the plastic that allows the fragrance material to be held initially with the plastic material that is used to form the body 11 of the urinal screen 10, then slowly released into the surrounding air during use of the screen. For example, the fragrance material may be absorbed into the plastic. Alternatively, it may be coated on the plastic.

The fragrance material can be any type suitable for masking offensive odors and/or for emitting pleasant odors. The fragrance material is sufficiently volatile to vaporize over time and be released from the urinal screen 10 into the surrounding air. In some embodiments, the fragrance material is a fragrance oil, also known as an aroma oil or an aromatic oil. Fragrance oils are synthetic aroma compounds or natural essential oils that may be diluted with a carrier such as benzyl benzoate, benzyl salicylate, tricyclodecanyl acetate, or any of a number of other carriers known in the art. Many different types of aroma compounds are known in the art, and they include compounds in different chemical groups such as acetates, alcohols, aldehydes, amines, esters, ethers, ketones, lactones, terpenes and thiols. Essential oils are hydrophobic liquids containing volatile aroma compounds from plants, and many different types are known in the art.

In some embodiments, the fragrance material does not function by emitting a pleasant odor, but rather it functions by acting as an odor neutralizer, an odor eliminator, and/or an odor counteractant. Some examples of odor counteractants are low-odor compounds, such as quaternary ammonium compounds, ricinoleate salts, cyclic organic compounds like cyclodextrines, specific odor neutralizers like Ordernone™ (from Belle Aire), crown ethers, etc. In some applications, it is preferred not to emit a fragrance to mask odors, but still to produce a malodor-free area. Alternatively, a material to neutralize, eliminate, or counteract odors could be included along with a material that emits a pleasant odor.

In contrast with current deodorizing urinal screen products that have a relatively low fragrance loading of typically 1-3% fragrance material by weight of the fragranced plastic, the urinal screen 10 of the invention can be produced with significantly higher fragrance loading. For example, the fragrance material can be included in an amount of from about 1% to about 75% by weight of the fragranced plastic, in some embodiments from about 5% to about 75% by weight, and in some particular embodiments from about 10% to about 75% by weight In some embodiments, the urinal screen 10 performs significantly better than current products in terms of fragrance release, particularly the total amount of fragrance released and also the percentage of fragrance released. For example, a current deodorizing screen made from polyvinyl chloride typically starts with a fragrance content of about 2 g (2.5% w/w) and releases about 0.8 g of fragrance oil over a 25 to 30-day period. A urinal screen 10 made with EVA according to the invention, of similar dimension to the current deodorizing screen, can start with a fragrance content of 17 g and release 14 g of fragrance oil over a 25 to 30-day period. In this example, the total amount of fragrance released by the urinal screen is 17.5 times (14 g versus 0.8 g) the amount of fragrance released by the current screen, which is a significantly improved performance. The urinal screen releases more fragrance than a premium metered aerosol product over the same time frame. Also in this example, the urinal screen 10 releases 82% of its original fragrance content, which is twice as much as the current screen which releases 42%. In some embodiments, the urinal screen 10 releases at least about 60 wt % of its initial fragrance content over a 30-day period, and more particularly at least about 70 wt %. In another aspect of the invention, the higher fragrance loading of the urinal screen 10 allows it to release fragrance into the surrounding area for at least about 25 days, in contrast with a current product having a lower fragrance loading that stops deodorizing in a much shorter period of time.

In some embodiments, one or more active ingredients are also included with the plastic and the fragrance material in the body 11 of the urinal screen 10. An active ingredient is a material that improves the functionality of the air freshening article, for example, by allowing the article to serve additional functions, or by enhancing or supplementing the deodorizing function of the article. Some examples of active ingredients are bacteria, enzymes, cleaning chemicals, chelating agents, and any combinations thereof. Stabilized bacteria or enzymes can add a cleaning function to the urinal screen 10. For example, enzymes can consume uric acids which are a source of odors from the urinal. Stabilized bacteria can enhance the deodorizing and cleaning capabilities of the urinal screen 10 by consuming different compounds from the urine.

The active ingredient can be incorporated into the plastic in any suitable manner. For example, an enzyme can be mixed into an inert material such as diatomaceous earth that, in turn, is mixed into the heated plastic during production of the urinal screen. Alternatively, the plastic can be a water soluble type that can absorb the active ingredient.

In one aspect, the lower molding temperature of the urinal screen 10 allows the inclusion of active ingredients that cannot be included in screens molded at higher temperatures. For example, the lower molding temperature allows active ingredients such as stabilized bacteria and enzymes to be included that would be destroyed or inactivated at higher temperatures.

In addition to the plastic, the fragrance material and the active ingredient, the body 11 of the urinal screen 10 can optionally include other materials suitable for use in plastic articles. For example, the body 11 of the urinal screen 10 may include colorants, process aids, fillers and/or reinforcements.

Some examples of additives that could be included are cleaning chemicals to reduce hard water build-up in toilets and urinals, additives to remove scale and mineral deposits from drain lines, actives that create an active biofilm in drain lines to clean and reduce malodors at their source, etc.

In one embodiment, the body 11 of the urinal screen 10 further includes a colorant such as a dye that helps to indicate when the screen should be replaced after a period of use. For example, a special dye could be used that is faded by light over 3-4 weeks to help indicate replacement.

The materials for producing the screen body may be selected to produce a urinal screen 10 having a desired appearance or other properties. For example, the use of EVA can allow the production of a translucent urinal screen 10 so that when the underside of the screen is dirty, it is visible and can be cleaned to control odors. Transparent urinal screens can also be produced. Also, a variety of different plastics and fragrance materials can be used to customize the urinal screen for particular applications. Different fragrance materials and loadings can be used depending on what fragrances are preferred and what fragrance performance (output) is desired for the application. The plastic can also be of environmentally or biologically friendly materials.

In one embodiment, the air freshening article shrinks over a period of time upon use of the article. This shrinkage can be an indicator of performance and also an indicator of when the article should be replaced. Current urinal screens do not shrink significantly upon use because they do not release much fragrance. In contrast, in one embodiment, the air freshening article of the invention shrinks considerably upon use, because it releases a significant amount of fragrance material and optionally active ingredient(s). The air freshening article can have any suitable amount of shrinkage, for example, it can shrink to about 60% to 90% of its original size (dimensionally) at approximately 30 days, and in some embodiments about 70% to 80%.

Figure 2:
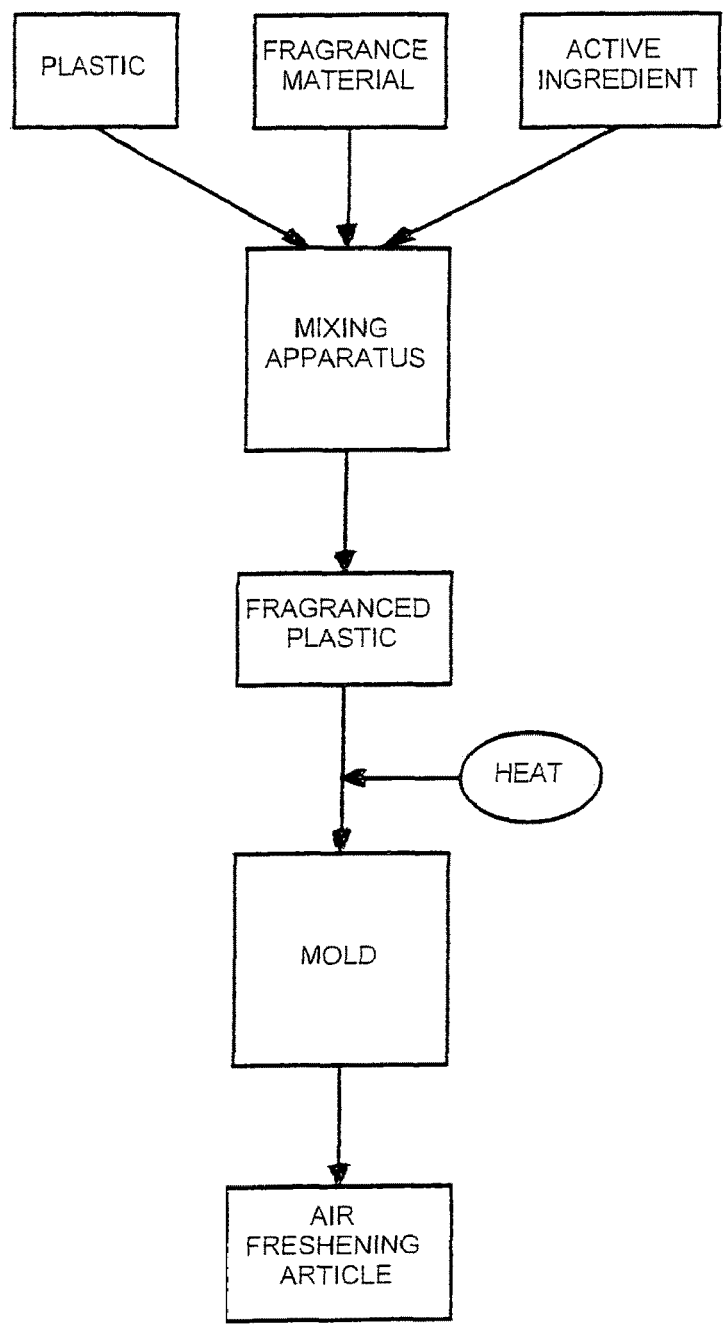
FIG. 2 is a flow chart of a method of manufacturing the air freshening article illustrated in FIG. 1.

The air freshening article of this invention can be formed by any suitable method, for example, by any of the methods known in the art for producing plastic articles, such as molding, stamping, casting, or extruding. In a particular embodiment, which is illustrated in FIG. 2, the air freshening article is produced in a multi-stage process that allows higher loadings of the fragrance material into the plastic. The loading of the fragrance material into the plastic is performed in a separate production stage, prior to a molding stage in which the fragranced plastic is molded into the air freshening article. This contrasts with currently known methods which load the fragrance into the plastic during the molding operation.

In the fragrance loading stage, a plastic is loaded with a fragrance material to produce a fragranced plastic. With this method, the incorporation of the fragrance material into the plastic is no longer performed during the molding operation. This change allows the product to contain a significantly higher fragrance load.

In addition, the implementation of a pre-molding fragrance loading stage may result in a significant reduction in the temperature of molding to manufacture the air freshening article. This makes the molding more efficient in terms of energy usage and also results in a reduced "burn off" of fragrance, which is a common problem caused by high molding temperatures. The pre-loading of fragrance into the plastic also creates an opportunity to utilize a variety of different plastics and different fragrances and loadings to customize the air freshening article for use in particular applications.

The fragrance loading stage can be conducted in any suitable manner. For example, the plastic can be provided in the form of beads or any other suitable form. As shown in FIG. 2, the plastic can be placed into any suitable mixing apparatus such as a mixing container. The plastic can then be heated until it softens. The fragrance material can then be added to the heated plastic in the container. Optionally, active ingredients or other suitable materials can also be added. The materials can all be heated and blended until the fragrance material and any other materials are loaded into the plastic. For example, the plastic may absorb substantially all of the fragrance material. FIG. 2 shows the production of a fragranced plastic from the mixing apparatus.

In some embodiments, the fragrance loading stage includes alternating cycles of the blending and the heating. Also, in some embodiments, the fragranced plastic produced in the fragrance loading stage is in a free-flowing form. This can be achieved, for example, by using a final blending step with no external heat.

In some embodiments, the heating during the fragrance loading stage is limited so that a high loading of the fragrance material is retained in the fragranced plastic. For example, the fragrance loading stage may be conducted at a temperature not greater than about 200° F., and more particularly not greater than about 175° F.

As shown in FIG. 2, after the fragrance loading stage, in a separate molding stage the fragranced plastic is molded into the air freshening article. Different molding processes and equipment are known in the art for molding plastic articles. For example, the molding processes include injection molding, compression molding, transfer molding, extrusion molding and blow molding. In one embodiment, the air freshening article is molded by an injection molding process. As shown in FIG. 2, the fragranced plastic is heated until melted and then injected at high pressure into a mold which is the inverse of the air freshening article's shape. The molded air freshening article is allowed to cool and harden and is then removed from the mold.

In one embodiment, the use of a low melting plastic allows the molding operation to be conducted at relatively low temperatures which help to retain the loading of the fragrance material in the plastic. For example, the molding operation may be conducted at a temperature not greater than about 250° F., and more particularly not greater than about 225° F.

The following example illustrates one method of producing a deodorizing urinal screen according to the invention. However, it is recognized that many other different methods or variations of the described method could also be used.

Step 1: 165 lbs of ethylene vinyl acetate resin (EVA) is placed into an open-head drum.

Step 2: The drum containing the EVA is heated to approximately 100° F.

Step 3: 165 lbs of fragrance oil is then added to the heated EVA resin. Dye is also added if desired.

Step 4: Additional active ingredients (e.g. stabilized bacteria) are also added to the drum.

Step 5: The contents of the drum are completely sealed.

Step 6: The contents are blended with various heating cycles at elevated temperature (100-150° F.) for specific timeframes. For instance, a polymer preparation cycle may start at room temperature and blend for 1 hour, then heat is applied to increase the temperature of the contents to 120° F., and the contents are blended for 1 hour. Heat is removed and the contents continue to be blended for 1-2 hours (material temperature is around 105° F.). The material is then heated again to approximately 125° F. and blended for an additional 1-2 hours. Final blending is performed with no external heat for 90 minutes, to insure free-flowing material is produced. Typically, at the end of this process, the resin is free-flowing and all of the fragrance oil has been absorbed into the EVA.

Step 7: The fragranced plastic is then introduced into the injection molding equipment. Urinal screens are molded from the free-flowing fragranced plastic at temperatures around 180° F.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A method of producing an air freshening article comprising the steps of:
    providing EVA having a melting point of not greater than 250° F.;
    in a fragrance loading stage, loading said EVA with from at least 15% to about 75% by weight of fragrance material to produce a fragranced EVA, said fragrance loading stage conducted at a temperatures such that said fragranced EVA is from at least 15% by weight fragrance upon completion of said fragrance loading stage; and
    in a molding stage subsequent to the fragrance loading stage, molding the fragranced EVA into a urinal screen comprising a screen body sized and shaped to be disposed over a urinal drain, said molding step comprising forming openings in said screen body, said molding stage conducted at a temperature such that said urinal screen is at least 15% by weight of fragrance material.

2. The method defined in claim 1 wherein the molding stage is conducted at a temperature not greater than about 250° F.

3. The method defined in claim 1 wherein the fragrance loading stage additionally comprises loading the EVA with an active ingredient comprising bacteria.

4. The method defined in claim 1 wherein the loading of the EVA with the fragrance material comprises absorbing a fragrance oil into the EVA.

5. The method defined in claim 1 wherein the fragrance loading stage comprises blending and heating the EVA and the fragrance material.

6. The method defined in claim 5 wherein the fragrance loading stage comprises alternating cycles of the blending and the heating.

7. The method defined in claim 1 wherein the fragrance loading stage produces the fragranced EVA in a free-flowing form.

8. The method defined in claim 1 wherein the fragrance loading stage is conducted at a temperature not greater than about 200° F.

9. The method defined in claim 1 wherein the molding stage comprises injection molding.

10. The method defined in claim 8 wherein the fragrance loading stage additionally comprises loading the EVA with an active ingredient comprising bacteria.

11. The method defined in claim 10 wherein the loading of the EVA with the fragrance material comprises absorbing a fragrance oil into the EVA.

12. The method defined in claim 10 wherein the fragrance loading stage comprises blending and heating the plastic and the fragrance material.

13. The method defined in claim 10 wherein the fragrance loading stage comprises alternating cycles of the blending and the heating.

14. The method defined in claim 10 wherein the fragrance loading stage produces the fragranced EVA in a free-flowing form.

15. The method defined in claim 10 wherein the molding stage comprises injection molding.

16. The method of claim 1, wherein the fragrance loading stage includes heating said EVA to a temperature not greater than 250° F.

17. The method defined in claim 1, wherein the molding stage is conducted at a temperature not greater than about 250° F.

18. The method defined in claim 1, wherein the fragrance loading stage additionally comprises loading the EVA with an active ingredient comprising an enzyme.

19. The method defined in claim 1, wherein said molding of the fragranced EVA comprises molding said fragranced EVA into a generally flat, circular one piece body.

20. The method defined in claim 19, wherein the molding stage is conducted at a temperature not greater than about 250° F.

* * * * *

UNITED STATES PATENT AND TRADEMARK OFFICE
CERTIFICATE OF CORRECTION

PATENT NO. : 8,007,707 B1
APPLICATION NO. : 12/152627
DATED : August 30, 2011
INVENTOR(S) : Brown et al.

It is certified that error appears in the above-identified patent and that said Letters Patent is hereby corrected as shown below:

In column 2 at line 45, remove the two paragraphs beginning at column 2 at line 45 and ending at column 2 at line 60.

In column 3 at line 67, change "tricyclodecanyl" to --tricyclodecenyl--.

Signed and Sealed this
Twelfth Day of February, 2013

Teresa Stanek Rea
*Acting Director of the United States Patent and Trademark Office*